United States Patent [19]
Gurfein et al.

[11] Patent Number: 5,611,973
[45] Date of Patent: Mar. 18, 1997

[54] PROCESS OF PRODUCING A STARTING MATERIAL IN THE FORM OF GRANULES

[75] Inventors: Veronique Gurfein, Le Plessis Robinson; Christian Zaffran, Suresnes; Eric Lapoirie, Villemonble, all of France

[73] Assignee: L'Oreal, Paris, France

[21] Appl. No.: 460,625

[22] Filed: Jun. 2, 1995

[30] Foreign Application Priority Data

Jun. 3, 1994 [FR] France ................................. 94 06843

[51] Int. Cl.$^6$ ....................................................... B29B 9/10
[52] U.S. Cl. .................................................. 264/5; 264/13
[58] Field of Search .................................... 264/5, 6, 7, 9, 264/13, 14

[56] References Cited

U.S. PATENT DOCUMENTS

| | | | |
|---|---|---|---|
| 3,721,725 | 3/1973 | Briggs et al. | 264/6 |
| 3,928,566 | 12/1975 | Briggs et al. | 424/94 |
| 4,594,075 | 6/1986 | Schenkenberger | 8/499 |
| 4,848,094 | 7/1989 | Davis et al. | |
| 5,384,124 | 1/1995 | Courteille et al. | |

FOREIGN PATENT DOCUMENTS

| | | |
|---|---|---|
| 0150158 | 7/1985 | European Pat. Off. |
| 58-056669 | 4/1983 | Japan. |
| A1146901 | 6/1989 | Japan. |
| WO90/13285 | 11/1990 | WIPO. |

*Primary Examiner*—David A. Simmons
*Assistant Examiner*—Kenneth M. Jones
*Attorney, Agent, or Firm*—Jacobson, Price, Holman & Stern, PLLC

[57] ABSTRACT

In a process for producing a starting material in the form of granules, the process includes:

(a) obtaining a dispersion or a solution, in a solvent or a mixture of solvents suitable for lyophilization, of a powdered starting material, the said dispersion or solution having a viscosity which makes it possible mechanically to form graded drops;

(b) mechanically forming graded drops from the said dispersion or solution;

(c) freezing the drops formed in Stage (b) in order to obtain frozen drops; and (d) lyophilizing the frozen drops obtained in Stage (c) in order to obtain micrporous anhydrous granules of the starting material having a regular shape and an even surface and of graded size.

10 Claims, No Drawings

PROCESS OF PRODUCING A STARTING MATERIAL IN THE FORM OF GRANULES

The present invention relates to a process for producing an anhydrous starting material in the form of microporous granules and to an anhydrous starting material in the form of microporous granules.

The invention also relates to the use of anhydrous starting material granules in the cosmetics, hair, veterinary or pharmaceutical field.

Starting materials in the pulverulent (powder) form, such as colouring materials, have various disadvantages related to the lack of particle size uniformity in these powders. A major disadvantage of this particle size non-uniformity in powdered starting materials is the presence of sometimes significant amounts of very fine particles which very frequently lead to safety and health problems due to the risk of atmospheric pollution by these very fine particles and of their deposition on factory walls.

This is in particular the case for toxic starting materials or dyes such as those used in cosmetics for dyeing the hair or the skin (make-up).

Moreover, these pulverulent starting materials generally flow with difficulty, which makes it difficult to handle them and in particular to weigh them during subsequent uses.

Finally, these pulverulent starting materials often require a relatively long solubilizing time when they are used in the manufacture of final solutions.

Consequently, it would be desirable to produce starting materials, such as colouring materials, in the form of granules, that is to say agglomerates of powder grains having a regular shape and an even surface and of graded size. These granules, which are less volatile than particles of powder, exhibit an appreciably reduced risk of atmospheric pollution and consequently of poisoning by inhalation via the respiratory tract, in the case of toxic starting materials.

Moreover, when the starting material is provided in the form of granules having a regular shape, an even surface and a graded size, it can easily be handled, especially owing to ease of flow, and in particular it is easy to carry out the precise automatic weighing thereof for subsequent uses.

Finally, by producing granules having a high microporosity, a starting material is obtained which is more easily dissolved than a starting material in the powder form.

Lyophilization is a known technique for obtaining anhydrous products which comprises the desiccation, by sublimation, of a product which has been solidified beforehand by freezing. This lyophilization is used for the manufacture of pharmaceutical, cosmetic, food or veterinary products in pulverulent form.

Published Japanese Patent Application JP 87 305 829 describes the preparation of a chitosan powder by dissolving chitosan in an acid, suspending, freezing and lyophilizing in order to obtain chitosan granules. Such a process does not make it possible to obtain granules with an even surface and with a homogeneous size.

Published Japanese Patent Application JP 81 152 449 describes a process for the production of a fine powder which consists in dissolving a vehicle substance in an alcoholic solvent, in spraying the solution in an atmosphere at a temperature of less than −40° C. in order to obtain frozen granulated fines and in drying the granules under vacuum while retaining them in the frozen state. Owing to the fact that the granules are formed by spraying by means of a propellent gas, the flow obtained is in the form of a more or less continuous thin stream and it is not possible to obtain frozen granules of homogeneous size.

The subject of the present invention is therefore a process for producing a starting material, and in particular colouring materials, in the form of anhydrous granules having a regular shape, an even surface and a graded size.

Another subject of the present invention is a process as defined above which provides granules having sufficient cohesion for their subsequent uses.

Another subject of the present invention is a process as defined above which provides granules having a microporous structure which facilitates subsequent dissolution of the product.

A further subject of the present invention is a starting material, such as a colouring material, in the form of anhydrous granules, with a regular shape, an even surface and a graded size, having a high porosity and thus exhibiting better solubilization than the powders.

The final subject of the present invention is the use of a starting material in the form of anhydrous granules in the cosmetics, hair, veterinary or pharmaceutical field.

According to the invention, a process for producing a starting material in the form of microporous anhydrous granules with a regular shape, an even surface and a graded size has been developed which consists in:

a) obtaining a dispersion or a solution, in a solvent or a mixture of solvents capable of being lyophilizable, of a powdered starting material, the said dispersion having a viscosity which makes it possible mechanically to form graded drops;

b) mechanically forming graded drops from the said dispersion or solution;

c) freezing the drops formed in Stage (b) in order to obtain frozen drops; and d) lyophilizing the frozen drops from Stage (c) in order to obtain granules of the starting material in the microporous anhydrous state having an even surface, a regular shape and a graded size.

In the present invention, the expression "starting material" encompasses single compounds, mixtures of compounds and finished or semi-finished products obtained from the single compounds.

A significant aspect of the process of the present invention relates to Stage (b) for mechanical formation of drops of graded size from the solution or dispersion of the pulverulent starting material. This stage is a mechanical shaping stage which, in contrast to other techniques such as spraying, makes it possible to obtain drops with a well-defined, generally spherical or semi-spherical, shape, an even surface and a graded size.

Processes and devices for the mechanical shaping of solutions and dispersions are known, among which may be mentioned devices comprising a simple manifold of pipes or needles, in which pipes or needles the solution or dispersion flows dropwise. These mechanical shaping devices can be manually, mechanically or electrically controlled.

The diameter of the drops formed depends on the type of equipment used, especially on the diameter of the pipe or needle at which the drop is formed (when a manifold of pipes or needles is used), and also on the nature of the optional additives added to the dispersion or solution. In general, the drops have a diameter of between 0.1 and 10 mm and preferably ranging from 1 to 5 mm.

The drops formed can comprise starting materials of different chemical natures and thus form a starting material in the form of granules having the characteristics of each of the starting materials.

The combination of granules comprising starting materials of different natures makes it possible to obtain a marketable product combining the intrinsic properties of the different granules comprising the starting materials.

The starting material can be provided directly in the form of a solution or of a dispersion in a suitable solvent or mixture of solvents, the viscosity of which can optionally be adjusted by the addition of a chemical agent or by the variation in a physical parameter, such as the temperature or the concentration of solid material. If the starting material is provided in the form of an anhydrous powder, it is then necessary to prepare a solution or dispersion of this powder in a suitable solvent or mixture of solvents.

The solutions or dispersions of pulverulent starting material used in the process according to the invention are obtained simply by dissolving or dispersing the powder in a solvent or mixture of solvents suitable for lyophilization.

Mention may be made, among solvents suitable for lyophilization which can be used in the present invention, of water, isopentane, dimethyl sulphoxide, methylamine, ethylamine, diethylamine, propylamine, fumaric acid, acetic acid, t-butyl alcohol, t-amyl alcohol, 1,4-dioxane, isobutane, ethylene oxide and cyclohexane. Water is recommended as sublimable solvent.

The solutions and dispersions used in the process of the invention must have a viscosity such that they can be mechanically shaped as drops. Consequently, the solids content of the solution or of the dispersion must be sufficient for this solution or this dispersion to have a viscosity suitable for pumping and for the formation of drops by the device intended for the formation of drops. Generally, this solids fraction is between 1 and 99% by weight with respect to the weight of the solution or of the dispersion.

In general, the solution or the dispersion has a viscosity not greater than 20 Pa.s and at least sufficient to make possible formation of drops with a defined size during the mechanical shaping stage. Preferably, the solution or the dispersion has a viscosity of between 0.001 and 15 Pa.s.

It is sometimes necessary to add one or a number of additives in order to obtain a viscosity which makes it possible mechanically to form graded drops and/or to confer a certain cohesion or degree of binding on the granules. These additives are generally chosen from the gelling agents and the structuring agents known in lyophilization. The structuring agents can optionally increase the viscosity of the solution or of the dispersion. The solutions and the dispersions according to the invention preferably contain both a gelling agent and a structuring agent.

Mention may be made, among the gelling agents which can be used in the solutions or dispersions according to the invention, of carbomers, hydroxyethyl cellulose, carboxymethyl cellulose, agar, xanthan gum, starch, polyethylene glycol, polyvinylpyrrolidone, locust bean gum, guar gum, gelatin, casein, pectin, alginates and carrageenates.

Mention may be made, among the structuring agents which can be used in the solutions or dispersions according to the invention, of mannitol, glucose, lactose, maltose, polyethylene glycol, starch, polyvinylpyrrolidone, inorganic salts, sorbitol and carbopol®.

The choice of the additive will very clearly depend on the subsequent use envisaged for the granules. The amount of additives can be easily determined by a person skilled in the art and depends on the additive chosen and on the degree of viscosity desired for the solution or the dispersion.

It is also possible to adjust the viscosity of the solution or of the dispersion by adjusting the temperature of the solution or of the dispersion during the mechanical shaping or alternatively by adjusting the percentage of solids in the solution or in the dispersion.

Generally, the viscosity of the solution or of the suspension can be adjusted, as desired, by a dilution, the addition of a gelling agent or by an increase and by a reduction in the temperature.

The graded liquid drops formed in the mechanical shaping stage can be frozen by any well-known process. In general, the freezing temperature of the solution or of the dispersion is between 0 and $-180°$ C.

The geometric shape of the drops obtained will depend on Stages b) and c) of the production process as defined above.

The frozen drops obtained are then subjected to a desiccation by sublimation (lyophilization) in order to remove the solvent or the mixture of solvents. This lyophilization can be carried out, for example, in a lyophilization chamber, as is well known. This removal by sublimation of the solvent or of the mixture of solvents from the frozen drops makes it possible for the granules formed to retain the shape of the starting frozen drops and thus makes it possible to obtain granules having a regular shape, an even surface and a graded size. Moreover, this lyophilization also confers an ordered microporous structure on the anhydrous granules.

In general, the granules obtained by the process of the invention have a high microporosity which is related to the rate of freezing (for example approximately 60% by volume of air and 40% by volume of solid).

The residual amount of solvents or of the mixture of solvents, at the end of the lyophilization, is preferably less than 3% by weight with respect to the total weight of the dry product.

This lyophilization is a well known and commonly used process, in particular in the food industry and the pharmaceutical industry.

The implementation of the process according to the invention therefore makes it possible to obtain an anhydrous starting material in the form of microporous granules with a regular shape, an even surface and a graded size. Indeed, the mechanical shaping stage makes it possible to obtain liquid drops with a predetermined and graded size which are then congealed by freezing. The lyophilization then makes it possible to retain the shape of the frozen drops and to obtain granules having a regular shape, an even surface, a graded size and a microporous structure.

In general, the granules obtained by the process of the invention have a mean diameter ranging from 0.1 to 10 mm and preferably from 1 to 5 mm.

The relative variation in weight between the granules obtained during the implementation of the process of the invention very obviously depends on the regularity in size of the liquid drops obtained during the mechanical shaping and on the homogeneity of the dispersion. Thus when use is made of a manifold system containing pipes or needles and of a homogeneous dispersion, it is possible to obtain a variation in weight between the granules of the order of 0.5%.

The granules obtained by the process according to the present invention are generally sufficiently cohesive to withstand handling. Good cohesion is generally obtained if the solution or dispersion contains a sufficient soluble fraction of the starting material that is to say a fraction greater in general than 0.5% by weight of the solids content.

The process of the invention is particularly suitable for the manufacture of starting materials for dyeing the hair and/or the skin (make-up), of liquid cosmetic products such as shampoos, of emulsions optionally containing pigments, of lyophilizable foodstuffs presented in the form of granules and of lyophilizable pharmaceutical products. The process of the invention is particularly useful for obtaining granules of colouring material. Appropriate dyes are the dyes conventionally used in cosmetics for dyeing the hair or the skin (makeup), such as azo, aromatic and anthraquinone dyes.

The starting material granules according to the invention generally have a spherical or semi-spherical shape or a flattened sphere shape and a mean diameter of between 1 and 10 mm and preferably between 1 and 5 mm, which facilitates the weighing and the use thereof. The high porosity of these starting material granules makes it easier to dissolve them for subsequent uses.

The regularity in size of the granules obtained makes it possible very accurately to measure out the starting materials such as colouring materials.

EXAMPLE 1

The following aqueous dispersion is prepared:

| | |
|---|---|
| para-Phenylenediamine or 1,4-diaminobenzene (dye) | 50 g |
| D-(−)-Mannitol (structurant) | 5 g |
| Carboxymethyl cellulose, sodium salt (gelling agent) | 0.15 g |
| Demineralized water q.s. for | 100 g |

The dispersion is prepared with atmospheric oxygen excluded. After homogenization, the dispersion has a viscosity of 0.29 Pa.s. It is shaped by dropping through a manifold of needles with an internal diameter of $2 \times 10^{-3}$ m.

The liquid droplets formed are frozen at 218° K. before being lyophilized at a temperature of 248° K. under a pressure of 30 Pa. The drying lasts approximately 20 hours.

The granules obtained have a mean weight of 15.5 mg and withstand a pressure of 22 kPa without being crushed. They generate less than 3% of particles with a diameter of less than $2 \times 10^{-3}$ m after agitating for 5 minutes.

EXAMPLE 2

The following aqueous dispersion is used:

| | |
|---|---|
| (Hydroxyanthraquinoneaminopropyl)methyl-morpholinium | 0.007 g |
| Oily compounds | 19 g |
| Preservative | 0.4 g |
| Maize starch | 3 g |
| Demineralized water q.s. for | 100 g |

The viscosity of this emulsion is sufficient to provide for shaping by dropping through a manifold of needles with an internal diameter of $2 \times 10^{-3}$ m without further addition of structuring agent and/or of gelling agent.

The liquid droplets are frozen at 218° K. before being lyophilized at a temperature of 253° K. under a pressure of 30 Pa. The drying lasts approximately 4 hours.

The granules obtained have the shape of flattened spheres and have a mean weight of 20 mg.

We claim:

1. Process for producing a starting material in the form of granules in the mircoporus anhydrous state having an even surface, a regular shape and a graded size, which consists in:
   (a) obtaining a dispersion or a solution, in a lyophilizable solvent or mixture of solvents of a starting material, said dispersion or solution having a viscosity which makes it possible mechanically to form graded drops;
   (b) shaping said dispersion or solution through a mechanical device so that said dispersion or solution flows dropwise from said device in the form of graded drops;
   (c) freezing in a freezing medium the drops formed in Stage (b) in order to obtain frozen drops; and
   (d) recovering from the freezing medium and lyophilizing the frozen drops obtained in Stage (c) in order to obtain granules of the starting material in the microporous anhydrous state having an even surface, a regular shape and a graded size.

2. Process according to claim 1, wherein the solution or the dispersion has a viscosity not greater than 20 Pa.s.

3. Process according to claim 2, wherein the dispersion or the solution has a viscosity of between 0.001 and 15 Pa.s.

4. Process according to claim 1, wherein, in Stage (a), the viscosity of the dispersion or of the solution is adjusted by diluting the solution or dispersion, adding a gelling agent to the solution or dispersion, or increasing or reducing the temperature of the solution or dispersion.

5. Process according to claim 1, wherein said gelling agent is chosen from carbomers, hydroxyethyl cellulose, carboxmethyl cellulose, agar, xanthan gum, starch, polyethylene glycol, polyvinylpyrrolidone, locust bean gum, guar gum, gelatin, casein, pectin, alginates and carrageenates.

6. Process according to claim 1, wherein a structuring agent is added to the solution or dispersion.

7. Process according to claim 6, wherein structuring agent is chosen from mannitol, maltose, glucose, lactose, polyethylene, glycol, starch, polyvinylpyrrolidone, inorganic salts, sorbitol and carbopol®.

8. Process according to claim 1 wherein the granules obtained are in a spherical or semi-spherical shape or in the shape of flattened spheres.

9. Process according to claim 1 wherein the granules obtained have a mean diameter of between 0.1 and 10 mm.

10. Process according to claim 9, wherein the granules obtained have a mean diameter of between 1 and 5 mm.

* * * * *